United States Patent
Wachinger

(10) Patent No.: US 9,964,527 B2
(45) Date of Patent: May 8, 2018

(54) SAMPLE PRE-COMPRESSION VALVE FOR LIQUID CHROMATOGRAPHY

(71) Applicant: DIONEX SOFTRON GMBH, Germering (DE)

(72) Inventor: Thomas Wachinger, Altomuenster (DE)

(73) Assignee: Dionex Softron GmbH, Germering (DE)

(*) Notice: Subject to any disclaimer, the term of this patent is extended or adjusted under 35 U.S.C. 154(b) by 127 days.

(21) Appl. No.: 15/190,570

(22) Filed: Jun. 23, 2016

(65) Prior Publication Data
US 2017/0219539 A1    Aug. 3, 2017

(30) Foreign Application Priority Data

Jan. 29, 2016   (DE) .................. 10 2016 101 658

(51) Int. Cl.
*G01N 30/20* (2006.01)
*G01N 30/02* (2006.01)

(52) U.S. Cl.
CPC ....... *G01N 30/20* (2013.01); *G01N 2030/027* (2013.01); *G01N 2030/207* (2013.01)

(58) Field of Classification Search
CPC .. G01N 30/20; G01N 30/24; G01N 2030/201; G01N 35/1097; G01N 2030/202
See application file for complete search history.

(56) References Cited

U.S. PATENT DOCUMENTS

| | | | |
|---|---|---|---|
| 3,530,721 A | 9/1970 | Hrdina | |
| 4,068,528 A * | 1/1978 | Gundelfinger | G01N 30/20 73/864.84 |
| 4,939,943 A | 7/1990 | Strohmeier | |
| 6,012,487 A * | 1/2000 | Hauck | F16K 11/0743 137/625.11 |
| 6,129,840 A | 10/2000 | Kitaoka | |
| 6,155,123 A * | 12/2000 | Bakalyar | G01N 30/20 73/61.55 |
| 6,382,035 B1 | 5/2002 | Nichols | |
| 6,475,391 B2 * | 11/2002 | Safir | B01D 15/08 210/635 |
| 7,503,203 B2 * | 3/2009 | Gamache | F16K 11/074 137/51 |
| 8,806,922 B2 * | 8/2014 | Hochgraeber | G01N 30/20 73/61.55 |
| 9,435,773 B2 * | 9/2016 | Glatz | G01N 30/20 |
| 2003/0098076 A1 * | 5/2003 | Nichols | F16K 11/074 137/625.46 |
| 2005/0194318 A1 * | 9/2005 | Ozbal | B01F 5/0085 210/656 |
| 2006/0042686 A1 * | 3/2006 | Gamache | F16K 11/074 137/51 |

(Continued)

*Primary Examiner* — David A Rogers
(74) *Attorney, Agent, or Firm* — Timothy J. Ohara

(57) ABSTRACT

A sample pre-compression valve for liquid chromatography applications is described. The valve enables a sample pre-compression while the solvent pump continues to conduct solvent to the chromatography column. Furthermore, the sample pre-compression valve includes an INJECT position, a LOAD position and a PUMP PURGE position, in which all connecting grooves of the valve are flushed with liquid. A use of the sample pre-compression valve is described as part of a sampler for liquid chromatography applications.

20 Claims, 8 Drawing Sheets

(56) References Cited

U.S. PATENT DOCUMENTS

| | | | |
|---|---|---|---|
| 2006/0191581 A1* | 8/2006 | Cueni | F16K 11/0743 137/625.46 |
| 2006/0260700 A1* | 11/2006 | Bauerle | F16K 99/0001 137/625.46 |
| 2007/0251302 A1* | 11/2007 | Iwata | G01N 30/20 73/61.56 |
| 2009/0145205 A1* | 6/2009 | Hochgraeber | G01N 30/20 73/61.55 |
| 2010/0288025 A1* | 11/2010 | Hochgraeber | G01N 30/20 73/61.55 |
| 2013/0067997 A1 | 3/2013 | Ebsen et al. | |
| 2014/0007660 A1* | 1/2014 | Moeller | G01N 30/20 73/61.56 |
| 2014/0197247 A1* | 7/2014 | Stearns | F04B 19/006 239/91 |
| 2014/0338431 A1* | 11/2014 | Hochgraeber | G01N 30/20 73/61.55 |
| 2014/0345371 A1* | 11/2014 | Hochgraeber | G01N 30/20 73/61.55 |
| 2014/0345372 A1* | 11/2014 | Gerhardt | B01L 3/502715 73/61.56 |

* cited by examiner

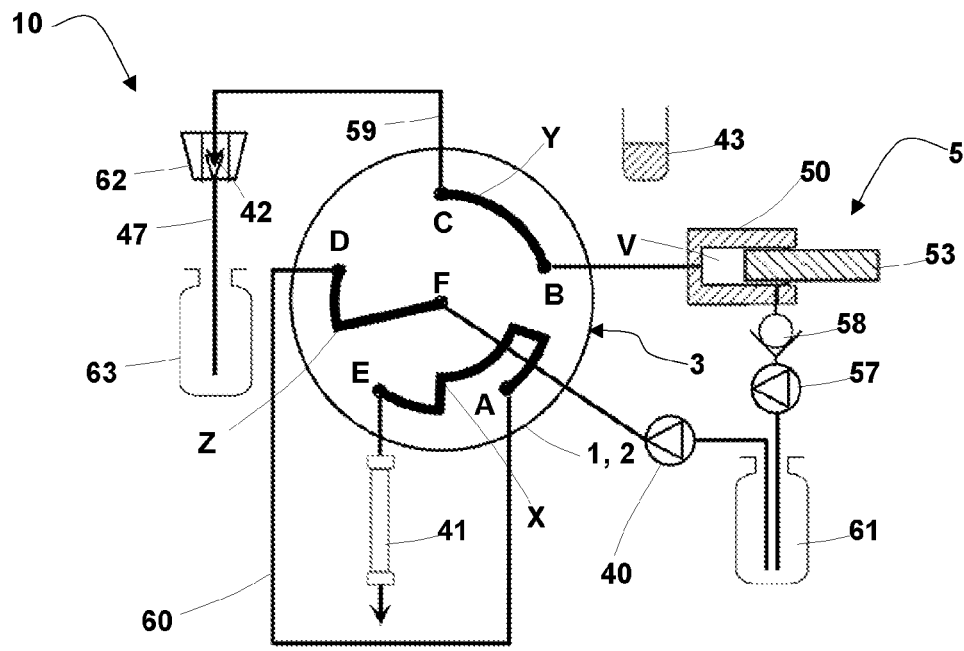
Fig: 3
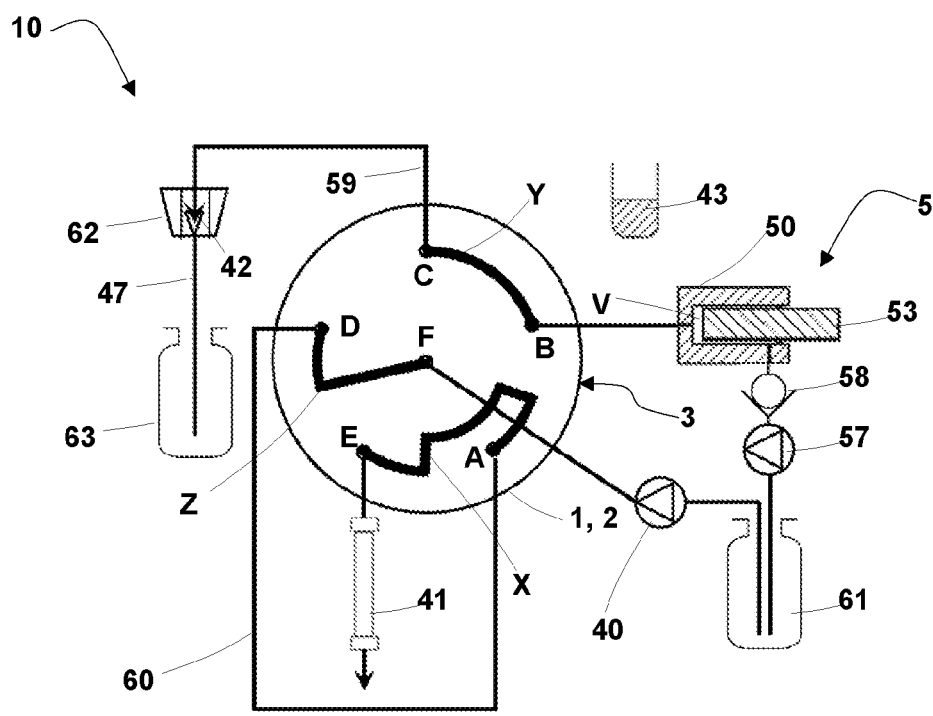
Fig. 4

US 9,964,527 B2

SAMPLE PRE-COMPRESSION VALVE FOR LIQUID CHROMATOGRAPHY

CROSS REFERENCE TO RELATED APPLICATIONS

This application is claims the priority benefit under 35 U.S.C. § 119 to German Patent Application No. DE 10 2016 101 658.6, filed on Jan. 29, 2016, the disclosure of which is incorporated herein by reference.

FIELD OF INVENTION

The present invention relates to a sample pre-compression valve for liquid chromatography applications.

BACKGROUND

In the HPLC, a sample to be analyzed must be fed into a high-pressure liquid flow; meanwhile, any interruption of this flow must be as short as possible. For this purpose, high-pressure injection valves are used that enable a nearly uninterrupted switching of the liquid flow. Such an arrangement is described, for example, in the U.S. patent specification U.S. Pat. No. 3,530,721 A.

The injection valves currently being used have at least four ports to be able to conduct a sample pre-compression by means of a sample conveying system. An additional port is needed when the solvent contained in the sample conveying system or a sample taken incorrectly is to be discarded through a waste port that is connected to the injection valve. A sampler with a corresponding injection valve is already described in DE 10 2008 006 266 A1.

When the solvent is changed in an HPLC system, it is necessary to flush out old solvent in the lines between the solvent bottles and the injection valve, likewise through the waste port. There is the possibility here, for example, to run the so-called injection needle directly over a waste tank and dispose the content of the line by means of the solvent pump. The disposal is generally referred to as a "purge." The previously mentioned change of solvent is described, for example, in U.S. Pat. No. 6,129,840 A.

Furthermore, with most of the injection valves in the state of the art, some connecting lines of a sampler are not completely flushed in the so-called injection position (INJECT position), meaning the position during which the sample is applied on the chromatography column. The connections that are embodied most frequently in the form of grooves in the stator or rotor of the injection valve are required to enable switching back and forth between the so-called load position (LOAD position; adding the sample to a sample loop of the injection valve) and the pressure compensation position (PRESSURE COMPENSATION position; position in which the sample loop is brought to system pressure or ambient pressure), yet also to enable switching back and forth between the LOAD position and the PRESSURE COMPENSATION position, without interrupting the solvent flow to the column. The flow must not be interrupted for the reason as the pump pressure would rise otherwise and the column pressure would drop enormously. The former is problematic for reasons of safety and the latter requires long equilibration phases between the sample analyses. The solvent that was used in the beginning of the chromatography run (e.g. in the equilibration phase) collects in the mentioned grooves and falsifies the gradient composition in the further course by mixing the solvent residue with the gradient (particularly critical in low-flow/nanoflow applications).

The problem to be solved by the present invention is therefore the provision of an injection valve with relatively simple arrangement to be used in a sampler for liquid chromatography applications, which can work with the fewest ports possible and the fewest grooves connecting the ports, while having a high density and no areas that are not flushed, and which can furthermore be produced at low cost, while the valve enables a pre-compression without an interruption of the solvent flow from the pump to the column arising in the transition from the LOAD position to the PRESSURE COMPENSATION position. Another problem to be solved is to provide an injection valve in which all grooves of the valve are flushed through completely in the INJECT position.

SUMMARY

The present invention relates to a sample pre-compression valve for liquid chromatography applications, in particular high-performance chromatography (HPLC), which enables a sample pre-compression while the solvent pump continues conducting solvent to the chromatography column. Furthermore, the sample pre-compression valve according to the invention enables an INJECT position, a LOAD position and a PUMP PURGE position, in which all connecting grooves of the valve are flushed through completely. The present invention also relates to the use of a sample pre-compression valve according to the invention for production of a sampler used in liquid chromatography applications. In addition, the present invention also relates to a sampler for liquid chromatography applications that includes a sample pre-compression valve according to the invention.

The invention solves the described problem by providing a sample pre-compression valve for liquid chromatography applications, which comprises a ring-shaped stator and a ring-shaped rotor, which are arranged next to each other along their circular surface and which can be rotated against each other along their circular surface, whereas the stator has at least five ports A, B, C, D and E and the rotor at least two grooves X and Y, whereas the grooves X and Y can connect respectively two of the ports A, B, C, D and E with each other and wherein the ports can be embodied point-shaped or groove-shaped, characterized in that (i) the groove X connects the ports A and B with each other in a valve position 1, in such a way that there are no dead volumes present in the groove X and so that the groove Y does or does not connect the ports C and D, and (ii) the groove X connects the ports A and B in a valve position 2, in such a way that there are dead volumes present in the groove X and so that the groove Y does or does not connect ports C and D, and (iii) the groove X connects the ports A and E with each other in a valve position 3, in such a way so that there are no dead volumes present in the groove X and so that the groove Y does or does not connect the ports B and C.

The groove Y preferably connects the ports C and D in position 1 of the sample pre-compression valve according to the invention. It is also preferred that the groove Y does not connect the ports C and D in position 2 of the sample pre-compression valve according to the invention. It is furthermore preferred that the groove Y connects the ports C and B in valve position 3. In this way, it is possible that the sample pre-compression valve according to the invention enables in position 1 that the sample is added to a sample loop of the injection valve (LOAD position); meanwhile also a solvent pump can be connected with a chromatography column. In that the groove Y does not connect the ports C and D in position 2 but the groove X connects the ports A and B, a so-called PRESSURE COMPENSATION position can be produced, in which the sample loop is brought to system pressure or ambient pressure and the solvent pump continues to supply the chromatography column. Position 3 enables an INJECT position in which the sample is applied on the chromatography column.

The sample pre-compression valve according to the invention is designed in such a way that there are no dead volumes present in the connecting grooves in positions 1 and 3 (LOAD and INJECT positions).

The term "sample pre-compression" expresses in the word "sample pre-compression valve" the suitability of the valve for sample pre-compression in a sampler used in liquid chromatography applications.

The ring-shaped stator and respectively the ring-shaped rotor are preferably circular discs that contact each other along their circular surface and can be rotated against each other along the rotation direction of their circular surfaces. In other words, the rotor has a front surface that interacts with the front surface of the stator (contacting surfaces of the stator and rotor), on which preferably (at least) the two grooves X and Y are arranged with which the port opening cross sections of the ports A, B, C, D and E, which are provided on the front surface of the stator, are connected or blocked respectively pressure-tight and preferably depending on the rotation position of the rotor relative to the stator.

A port can be understood to mean a point-shaped port or groove-shaped port. A point-shaped port is understood to mean a circular hole or a circular recess, whereas a groove-shaped port is understood to mean one that has a certain extension direction in the stator. If a port is a groove-shaped port, it is preferable according to the invention that the groove extends along a circular path around the center of the ring-shaped stator.

"Dead volumes" is understood to mean a part of a groove that cannot be flushed in one flow in a certain valve position. Vice versa, "no dead volumes" is understood to mean that essentially all parts of the relevant groove are flushed in a certain valve position.

In one embodiment of the sample pre-compression valve it is preferable that the ports A and B are arranged on one or two (preferably one) circular path(s) around the center of the ring-shaped stator. However, it can also be preferable according to the invention that port A is arranged at the center of the ring-shaped stator and port B on a circular path around the center of the ring-shaped stator.

In the sample pre-compression valve according to the invention, ports C, D and E can be arranged on one or more (preferably one) circular path(s) around the center of the ring-shaped stator.

In a variant of the sample pre-compression valve according to the invention, the ports A, B, C, D and E are preferably arranged on the same circular path around the center of the ring-shaped stator. In a further variant, the ports B, C, D and E can be arranged on the same circular path around the center of the ring-shaped stator. In the variant mentioned last, it can be preferred that port A is arranged at the center of the ring-shaped stator.

In the following, the sample pre-compression valve according to the invention will be described by means of two different embodiments, the preferred characteristics of which, however—to the extent they are technically feasible—are transferable to the respective other embodiment.

In the first embodiment of the sample pre-compression valve it is preferable that the ports A and B are arranged on one or two (preferably one) circular path(s) around the center of the stator. It is furthermore preferred that the stator has an additional port F, besides the ports C, D and E, which is arranged at the center of the ring-shaped stator. Preferably, the ports C, D and E are also arranged on a circular path around the center of the ring-shaped stator.

In addition, the sample pre-compression valve according to the invention in the first embodiment can comprise a further groove Z in the rotor, which can connect port F with one of the ports A, B, C, D or E. It is particularly preferred that the groove Z in position 1 connects the ports E and F with each other in such a way that no dead volumes are present in groove Z. It is also preferred that the groove Z in position 2 connects the ports E and F with each other in such a way that dead volumes are present in groove Z. Likewise preferred is that the groove Z in position 3 connects the ports D and F with each other in such a way that no dead volumes are present in groove Z.

In a position 4 of the sample pre-compression valve according to the invention in the first embodiment, it is furthermore preferred that the groove X connects the ports D and E with each other in such a way that no dead volumes are present in groove X. It is also preferable in this position 4 that the groove Z in position 3 connects the ports C and F with each other in such a way that no dead volumes are present in groove Z. It is thereby possible with the sample pre-compression valve according to the invention to implement a so-called PUMP PURGE position, in which the groove Z is flushed through completely with solvent by means of a solvent pump.

With the sample pre-compression valve according to the invention in the first embodiment, also a position 5 can be implemented in which the groove X connects the ports B and C with each other in such a way that no dead volumes are present in groove X, while the groove Y does or does not connect and preferably connects the ports D and E. This position 5 facilitates the provision of a sampler with the sample pre-compression valve according to the invention, having an INJECT position that is an alternative to position 3. In this position, it is furthermore preferred that the groove Z connects the ports A and F with each other.

In the first embodiment, the ports A, B, C, D and E are preferably arranged on one single circular path around the center of the ring-shaped stator. It is preferred here that all spaces between the ports are equally far away from each other.

The groove X is preferably a groove that has at least two circle-path-shaped sections that are preferably arranged on the same circular path and connected by one section of the groove that is arranged outside of this circular path.

The groove Y is preferably a circle-path-shaped (arched) groove or a line-shaped groove that can connect two points on the same circular path.

The groove Z is preferably a hook-shaped groove and preferably designed in such a way that one section of the groove connects the center of the ring-shaped rotor with one point on the circular path of the rotor and a further section of the hook-shaped groove is arranged on said circular path, meaning it is designed as an arched shape.

In the first embodiment of the sample pre-compression valve according to the invention it is furthermore preferable that the valve has at most six ports. It is furthermore preferred that these at most six ports are arranged in the stator of the valve. It is furthermore also preferred that the rotor has at most three grooves.

In the second embodiment of the sample pre-compression valve according to the invention, it is preferred that port A is arranged at the center of the ring-shaped stator. In addition, port B is preferably arranged on a circular path around the center of the ring-shaped stator. Likewise, the ports C, D and E are preferably arranged on one or more circular path(s) around the center of the ring-shaped stator. It is particularly preferable that the ports B, C, D and E can be arranged on the same circular path around the center of the ring-shaped stator.

In positions 1 and 2 of the sample pre-compression valve according to the invention in the second embodiment, the port E is preferably connected with none of the grooves X and Y. It is furthermore also preferred that the port D is connected with none of the grooves X or Y in positions 2 and 3.

It is furthermore preferred for the sample pre-compression valve in the second embodiment that it has at most five ports. The reduction to a maximum of five ports in the second embodiment has the advantage of a simplified arrangement and it reduces the leakage rate compared to an injection valve with six or more ports.

It is also preferred in the second embodiment that the port A is essentially spaced equally far away from the ports B, C, D and E. The expression "essentially" is to clarify that there can only be differences in the spacing here that are due to processing technology, which however do not affect the functionality of the injection valve. It is also preferred that the ports C and E are arranged on opposites sides relative to the port A and that both are essentially spaced equally far away from the ports B and D respectively. The word "essentially" has the same meaning here as above.

According to the invention, it is also possible that the sample pre-compression valve in the second embodiment has more than two grooves. However, it is particularly preferred according to the invention that the valve has at most the two mentioned grooves. The maximum number of two grooves has the advantage that the leakage rate in the valve can be kept very low.

The groove X in the second embodiment preferably has a hook-shape, whereas the groove Y is preferably designed line-shaped or arched, whereas the two end points are respectively arranged on a circular path around the center of the ring-shaped rotor. The two grooves preferably extend in the direction of the interacting front surfaces of the rotor and stator. The terms "hook-shaped" or "circle-path-shaped" are understood in the same way as for the first embodiment.

The sample pre-compression valve according to the invention in the second embodiment likewise has a position 4, in which the groove X connects the ports A and D with each other in such a way that no dead volumes are present in groove X. At the same time, it is preferred in this position 4 that the groove Y connects the ports B and E with each other.

The sample pre-compression valve according to the invention in the second embodiment can also have a position 5, in which the groove X connects the ports A and C with each other in such a way that no dead volumes are present in groove X. In this position, it is also preferable that the groove Y connects the ports D and E with each other.

The sample pre-compression valve according to the invention in the first embodiment can also have a position 6, in which the groove X connects the ports A and C with each other in such a way that there are dead volumes present in groove X. In this position 6 it is furthermore preferred that the ports B, E and D do not have a connection with a further port. In other words, the groove Y does not connect any of the other ports in this position.

The hook shape of the groove Z in the first embodiment and of the groove X in the second embodiment, which extends into a circular path in one section from the central port, has the advantage that the contact surface between the stator and rotor is moistened during the switching of the valve. The lifetime of the valve is thereby increased.

The present invention also relates to a sampler for liquid chromatography applications, which comprises, besides the sample pre-compression valve according to the invention, a sample conveying system, a sample loop, a solvent pump, a chromatography column and a sample intake/discharge line.

Furthermore, the sampler according to the invention preferably has a control unit for actuation of the sample pre-compression valve and the sample conveying system.

The sample conveying system can preferably also be provided with a movable element that is guided sealed in a pump volume and can be moved for conducting the sample fluid contained in the pump volume by means of one of the drives of the sample conveying system, which can be actuated by the control unit.

The sample conveying system is preferably designed high-pressure resistant and can generate pressures that are used in high-performance liquid chromatography, preferably pressures greater than 500 to 600 bar, preferably maximum pressures greater than 1500 bar.

If the sampler according to the invention has a sample pre-compression valve in the first embodiment, it is preferred that port A is connected with port D through the sample loop, port B is connected with the sample conveying system, port C with the sample intake/discharge line, port E with the chromatography column and port F with the solvent pump. This way, the following functionalities result in positions 1 to 5 for the sampler with the sample pre-compression valve according to the first embodiment:

Position 1: INJECT position
Position 2: PRESSURE COMPENSATION position
Position 3: LOAD position
Position 4: PUMP PURGE position
Position 5: INJECT position (alternative)

In the LOAD position, the sample can be taken in the sample loop through the sample intake/discharge line, in that a certain volume is aspired by the sample conveying system. This is possible because the grooves X and Y and the sample loop connect the sample conveying system with the sample intake/discharge line. For the intake of the sample, the sample intake/discharge line is led into a sample tank, preferably in that a needle that is dipped into the sample is seated on the end of this line. While this way, the sample can be drawn up into the sample loop in the LOAD position, solvent can be conducted through the groove Z from the solvent pump to the chromatography column.

After the LOAD position, the sample pre-compression valve according to the invention can be brought into the PRESSURE COMPENSATION position, in which the solvent pump is still connected with the chromatography column through the groove Z, but in which the port D is closed pressure-tight. The groove X continues to connect the ports A and B, so that pressure can be built up in the groove X and the sample loop through the sample conveying system, which pressure equals the later column pressure. This is also referred to as the pre-compression, before the valve is brought into a switching position and in which the sample can be applied on the chromatography column. During this step, it is furthermore beneficial if the needle is brought out of the sample into a so-called wash port at the end of the sample intake/discharge line.

If the sample pre-compression valve according to the invention in the first embodiment is brought into the INJECT position after the PRESSURE COMPENSATION position, pressure equaling or approximating the working pressure on the chromatography column and respectively the pressure in the pump line is already present in the PRESSURE COMPENSATION position from the sample pre-compression. In this position, the grooves X and Z enable the solvent pump to conduct the sample including solvent to the chromatography column. In the INJECT position, the sample conveying system, the groove Y and the sample intake/discharge line can be flushed through the groove Y, which connects the ports B and C. It is preferred here that a cleaning pump, flushing the cleaning fluid into the wash port through the sample conveying system, the line that connects the sample conveying system with the port B, the groove Y and the sample intake/discharge line are arranged on the sample conveying system.

The sample pre-compression valve according to the invention in the first embodiment thereby has the advantage that in all three positions, which are the LOAD, PRESSURE COMPENSATION and INJECT positions, the pump can convey solvent (with or without sample) to the chromatography column. It is possible at the same time to conduct the sample pre-compression in the PRESSURE COMPENSATION position.

After the INJECT position, the valve can be brought back into the PRESSURE COMPENSATION position, in which the sample loop that is under high pressure is connected with the sample conveying system that is under atmospheric pressure. Since the liquid volume of the sample conveying system is preferably much higher than that of the sample loop, the connected pressure surge related thereto can be absorbed without complications. After the decompressing phase of the sample loop by means of the sample conveying system, the valve can be brought into position 1 (equivalent of the LOAD position), in which the remaining pressure can be let off into the wash port through the sample intake/discharge line and its needle. After this pressure reduction, the valve is already in position 1, which is equivalent of the LOAD position and in which a sample can be drawn again for a repeated analysis run. For this purpose, the valve itself does not need to be activated, but the needle on the sample intake/discharge line must be taken out of the wash port and led into the sample tank. Subsequently, the steps described above can be repeated.

A sampler with a pre-compression valve according to the invention of the first embodiment has the following advantages: No pressure drop occurs on the chromatography column between the analysis runs. The valve has maximum tightness because the grooves are arranged with a greatest possible spacing between them. A sample pre-compression is possible between the taking of the sample and injection of the sample into the chromatography column. Analysis time can be saved, as a wash phase is possible during the analysis run. By virtue of the arrangement of the sampler according to the invention, a sample taken incorrectly that is not supposed to reach the chromatography column can be discarded easily. The idle volume is dependent only on the sample loop and therefore low and constant. No uncontrolled pressure reduction can occur when the sample conveying system is disconnected from the analysis path. In the LOAD position and in the INJECT position, there are no dead volumes in the grooves, i.e. all grooves can be flushed.

Consecutive switching states of the sample pre-compression valve are nearest neighbors so that no unintended connections occur and the contact travel can be kept low.

The sampler with the sample pre-compression valve according to the invention in the second embodiment furthermore preferably comprises a sample loop with sample conveying system and needle seat, a discharge line, a solvent pump and a chromatography column. It is preferred here that port A is connected with the solvent pump, port B connected with the chromatography column, port C with the sample loop and port D with the discharge line.

In this arrangement, positions 1 to 6 correspond to the following states:

Position 1: LOAD position
Position 2: PRESSURE COMPENSATION position
Position 3: INJECT position
Position 4: PUMP PURGE position
Position 5: FULL PURGE position
Position 6: UNDERPRESSURE position The sample loop in the sampler according to the invention with the sample pre-compression valve according to the invention in the second embodiment comprises a first and a second sample loop segment. The first sample loop segment is preferably connected on one end with the port E and on the other end with a pump volume of the sample conveying system. The second sample loop segment is preferably connected on one end with the port C and on the other end with the sample conveying system. The second sample loop segment is preferably an intake part and a feed part designed so that it can be split up, whereas in the split state volume, the free end of the intake part connected with the pump can aspire a sample fluid, which can be conveyed through the feed part in the connected state in the direction toward port E.

In the LOAD position, the two ports A and B are connected with each other so that solvent can be conducted from the solvent pump to the chromatography column. It is preferred at the same time that ports C and D are connected with each other, so that the sample drawn up in the intake part can be injected into the feed part of the sample loop.

According to the invention, the sample pre-compression valve, after aspiration of the pump volume in the LOAD position, is switched to the PRESSURE COMPENSATION position in which the ports C and E are closed pressure-tight. In the PRESSURE COMPENSATION position, the drive of the sample conveying system is actuated preferably so that pressure builds up in the closed sample loop and in the pump volume of the sample conveying system, which is essentially equivalent of the system pressure. Even if before switching the sample pre-compression valve from the PRESSURE COMPENSATION position to the INJECT position, the pressure in the sample loop is not identical to the system pressure of the pump(s) but a low pressure difference remains, this low pressure difference is kept low enough according to the invention, so that the pressure difference cannot have any impermissible negative effects on the flow through the chromatography column or even lead to damage on the injection valve or the chromatography column. This applies in the same way also in the LOAD position of the sampler with injection valve according to the invention in the first embodiment.

After the PRESSURE COMPENSATION position, the sample pre-compression valve is brought into the INJECT position, in which the solvent pump is connected via the groove X and the ports A and E with the sample loop, and the port C of the sample loop via the groove Y with the port B of the chromatography column in a sampler with sample pre-compression valve of the second embodiment. This way, the sample drawn up by means of the solvent pump in the feed part of the sample loop can be conveyed to the chromatography column and the analysis run can take place.

Upon completion of the analysis run, the sample pre-compression valve of the second embodiment can be brought into the PUMP PURGE position, which is understood to mean a state in which the feed line is flushed with solvent from the pump to the port A connected with it, the port A itself is flushed as well as the groove X between the port A and the port D, and the port D itself, whereby they can be cleaned and solvent can be disposed of.

After the PUMP PURGE position, the sample pre-compression valve in the second embodiment can be brought into a FULL PURGE position, which is understood to mean a state in which all grooves and ports of the sample pre-compression valve (with exception of port B that is connected with the chromatography column), as well as all intake and discharge lines, sample loops and the sample conveying device are flushed with solvent preferably by means of a pump whereby they can be cleaned. Furthermore, also the sample needle from the outside and the injection port can be washed in the FULL PURGE position of the sample pre-compression valve. For this purpose, the sample needle is extended slightly out of the needle seat (also referred to as injection port), so that the solvent conveyed from the pump will wash away contaminations on the outside of the sample needle and on the needle seat. The soiled solvent can then run, for example, through an overflow on the needle seat into a waste tank.

In addition, the sample pre-compression valve according to the invention in the second embodiment enables an UNDERPRESSURE position in a sampler according to the invention, in which the groove X preferably connects the ports A and C with each other, whereas the ports E and B are closed pressure-tight. This position has the advantage that underpressure in the sample loop and up to the pump can be created. This underpressure can be created in that the pump volume of the sample conveying device is increased, preferably in that a movable element (piston) of the sample conveying device is moved toward the outside. The creation of the underpressure helps support the pump when the solvent is aspired, in that the hydrostatic column of the solvent in the solvent bottles is overcome. The UNDERPRESSURE position furthermore enables enlarging unwanted gas bubbles so that these can be removed from it more easily.

Said designs of the grooves and ports in the sample pre-compression valve of the second embodiment of the sampler according to the invention have the advantage that all parts of the grooves and ports can be flushed in nearly all switching position (except for the PRESSURE COMPENSATION and UNDERPRESSURE positions). In other words, there are nearly no areas in the injection valve that cannot be flushed, whereby good cleaning is possible and no modifications in the running behavior caused by contaminations occurs in the HPLC operation.

It is furthermore preferable according to the invention that the sample pre-compression valve of the second embodiment has at most the specified six positions, notably the LOAD position, the PRESSURE COMPENSATION position, the INJECT position, the PUMP PURGE position, the FULL PURGE position and the UNDERPRESSURE position, preferably to implement all necessary states in a sampler for an HPLC. According to the invention, all specified positions can be realized by the two aforementioned grooves in the injection valve. The sample pre-compression valve in the second embodiment of the sampler according to the invention is preferably arranged in such a way that it can be brought into said positions by rotation in the following order: LOAD position→PRESSURE COMPENSATION position→INJECT position→PUMP PURGE position→FULL PURGE position→UNDERPRESSURE position→LOAD position. This has the advantage that it can be transitioned directly from the respective switching position to the respectively required next switching position, without unwanted intermediate switching positions. This does not cause any sample losses, no unwanted mixing with potential residues in the ports that would otherwise come into contact through the intermediate switching positions and no unwanted pressure drop occurs.

An additional advantage of the valve arrangement in the second embodiment of the sampler according to the invention is that, depending on the switching position of the valves, nearly all existing parts can be flushed by means of the solvent pump(s). It is therefore furthermore preferred that the sampler according to the invention has at most one (solvent) pump path. The pump path is understood to mean here the connection line from the solvent pump(s) to the port A. The sampler according to the invention can thus not only comprise one solvent pump but also two or more solvent pumps, all of which can supply solvent to the relevant port. It is preferred according to the invention that the sampler includes no further cleaning pump besides the solvent pump (s), as the cleaning can take place while the solvent is being conveyed through the solvent pump(s) by virtue of the different injection valve switching positions.

The sampler according to the invention with the sample pre-compression valve of the second embodiment has the advantage that the integration of a sample conveying system enables a pressure compensation is created by the sample conveying system in the split loop while the switching positions of the pre-compression valve are changed, if the valve has a PRESSURE COMPENSATION position for this purpose, in which the ports to which the sample loops are connected are not connected with other ports in the valve.

Under the split loop principle, the sample loop is split in the connecting part between the sample conveying system, which can be designed, for example, as a syringe, and the relevant port of the valve. The end of the intake part connected with the sample conveying system of the split connecting part of the sample loop is moved to a sample tank to take in the necessary sample volume or to a flushing medium tank to take in the flushing medium. In the end, the split connecting piece of the sample loop is connected again so that the sample volume taken in can be injected into the chromatography column by means of the pump(s) while the injection valve is in the INJECT position. This basic principle has already been described in U.S. Pat. No. 4,939,943 A1.

The pressure compensation (pressure increase or pressure reduction) in the sample loop of the sampler according to the invention with a valve of the first and second embodiment is preferably achieved by means of a corresponding actuation of the sample conveying system drive. This way, no interfering fluid flows arise in the pressure compensation. The sampler additionally has the advantage that the pump continues to be connected with the chromatography column in the PRESSURE COMPENSATION position. The flow of the fluid through the chromatography column is thereby preserved and no unwanted peaks in the pressure flow can arise in the switching processes.

Furthermore, the FULL PURGE position of the sample pre-compression valve of the second embodiment has the advantage that both the sample loop as well as port A that is connected to the pump, the two ports C and E that are connected to the sample loop, the port D and the sample conveying system can be flushed by means of the solvent pump without requiring that the sampler has an additional cleaning pump. The PUMP PURGE position has the advantage that the sample pre-compression valve of the second embodiment can also have a position in which the port A and the port D that are connected to the solvent pump are flushed.

In all variants of the sampler according to the invention, the sample conveying system comprises a movable element by means of which the volume of the sample conveying system can be altered. The movable element can be designed, for example, as a driven syringe, whereas the movable element is formed by the piston of the syringe.

Once the PRESSURE COMPENSATION position of the respective injection valve is reached, the control unit can move the piston and respectively the movable element by means of a corresponding actuation of the drive, along a predefined path that is sufficient in order to generate the necessary alteration of the pump volume of the sample conveying system through elasticities of the devices conducting the fluid and through the compressibility of the fluid itself, whereas increasing the pump volume can reach a pressure reduction in the sample loop essentially down to ambient pressure and a pressure increase in the sample loop essentially to the operating pressure of the pump. The movement of the movable element can be actuated and respectively controlled.

To enable the pressure regulation or the final pressure during the pressure compensation in the sample loop, a pressure sensor can be provided that records the pressure of the fluid in the closed sample loop or in the pump volume of the sample conveying system, at least during the time in which the injection valve is in the PRESSURE COMPENSATION position.

In this variant, the signal of the pressure sensor is preferably led to the control unit, whereas the control unit compares the fluid pressure to the target pressure value and actuates the sample conveying system in such a way that the pressure of the fluid reaches a high-pressure target value before the injection valve is switched from the PRESSURE COMPENSATION position to the INJECT position and/or so that the fluid pressure reaches a low-pressure target value before the injection valve is switched from the PRESSURE COMPENSATION position to the LOAD position.

The sampler according to the invention with the sample pre-compression valve of the second embodiment can preferably have a waste line, which leads from port D to a tank surrounding the needle seat or to the needle seat itself. According to the invention, the needle seat is one with a rinsing function. If the sample needle is slightly driven out of the needle seat in the FULL PURGE position, the conducted solvent can wash off the sample needle from the outside. At the same time, the needle seat with rinsing function preferably has an overflow from which the solvent can drain into a waste tank.

Analogously, a sampler with the sample pre-compression valve of the first embodiment can have a wash port, in which the needle that is arranged on the sample intake/discharge line can be washed. Here, too, the wash port is designed as a tank into which the needle can be dipped. The wash port comprises a line that can conduct the solvent used for cleaning into a waste tank.

The present invention also relates to the use of a sampler according to the invention in the liquid chromatography, specifically in the high-pressure liquid chromatography. In other words, the present invention relates to a method for conducting liquid chromatography in application of a sampler according to the invention, in particular by means of transitioning the positions of the sample pre-compression valve of the sampler according to the invention in the ways described above. In the use of the sampler according to the invention, the pump(s) for conducting the solvent/fluid is (are) preferably also used as cleaning pump, in particular in the PUMP PURGE position and the FULL PURGE position, which applies specifically to an injection valve of the second embodiment.

BRIEF DESCRIPTION OF THE DRAWINGS

The invention is explained in more detail by means of two embodiment examples illustrated in the drawings.

FIG. 3 is the HPLC system according to FIG. 1 and FIG. 2, which has been switched to the INJECT position.

FIG. 4 is the HPLC system according to the foregoing Figures, whereas the sample pre-compression valve is in the same position as in the INJECT position but where the rinsing phase is shown during the analysis run.

DETAILED DESCRIPTION OF THE EMBODIMENTS

In the following, a sampler according to the invention with a pre-compression valve of the first variant is described by means of FIGS. 1 to 8.

Figure 1:
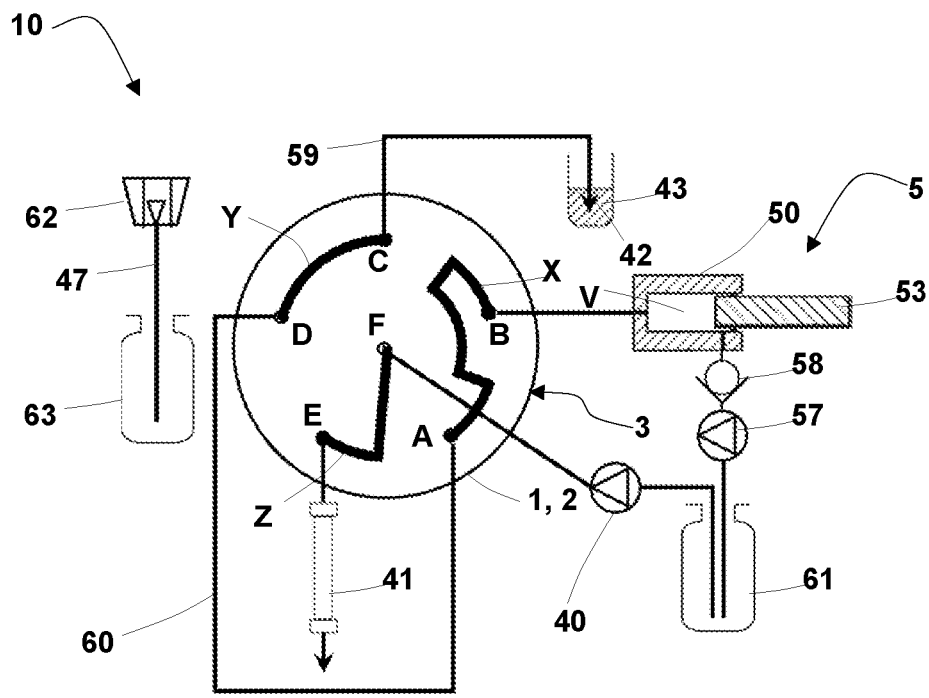
FIG. 1 is a schematic diagram of an HPLC system with a sampler according to the invention with a sample pre-compression valve of the first embodiment in the LOAD position.

FIG. 1 shows a schematic diagram of an HPLC system for samples in the nano-liter range with a sampler 10 according to the invention, which comprises a sample conveying system 5, a sample pre-compression valve 3 and a pump, preferably a high-pressure pump 40. In addition, the sampler 10 comprises a sample loop 60, a chromatography column 41, a cleaning pump 57, a return valve 58, and a sample intake/discharge line 59 with a sample needle 42 on its end, and a sample tank 43, a solvent bottle 61, a wash port 62 with a waste line 47 leading to the waste tank 63. The sample pre-compression valve in FIG. 1 is in the LOAD position, in which the groove X connects the ports A and B, the groove Y connects the ports C and D and the groove Z connects the ports E and F with each other. Furthermore, the sample needle 42 that is mounted on the end of the sample intake/discharge line 59 is arranged in the sample tank 43. If the piston 53 of the syringe 50 is pulled toward the outside of the sample conveying system 5, the volume V increases and a sample is taken up into sample loop 60 via the connection of the ports D and C via the grooves X and Y and the sample loop 60. In this position, the chromatography column 41 can be flushed through the connection of the ports E and F via the groove Z by means of a solvent pump 40 that is connected with a solvent bottle 61. The sample loop can be a pressure-resistant line with a small diameter, for example, in the form of glass or stainless steel capillaries.

The sample pre-compression valve 3 is preferably comprised of a stator 1 and a rotor 2. Whereas, stator 1 is preferably provided with the ports A, B, C, D, E and F. These ports connect the sample pre-compression valve 3 with the other functional elements of the HPLC element through the connecting lines described above, which can be embodied as capillary connections. In the interest of clarity, the high-pressure screw connections required for this purpose are not shown in FIG. 1. For reasons of simplicity, the sample pre-compression valve is shown in the border area between the stator 1 and the rotor 2, whereas both the design of the front face of the stator 1 as well as the design of the front face of the stator 2 is shown, to help understand the mode of functioning. Within the sample pre-compression valve 3, the ports are preferably embodied as drill holes leading to the other side of the stator. The rotor 2 as shown in the illustration of FIG. 1 comprises the grooves X, Y and Z, which are aligned precisely on the drill holes of the entry and exit ports.

The rotor 2 is preferably pressed against the stator with pressing force, so that a common border area between the rotor 2 and the stator 1 is formed where both parts tighten against each other. The pressing force is dimensioned for this purpose in such a way that the arrangement is still tight even under the highest expected pressures.

The sample conveying system 5 comprises a syringe 50 in the illustrated embodiment, in which a piston 53 is guided pressure-tight and movable. The piston 53 is powered by drive (not illustrated), for example, a step motor. The drive is preferably actuated by a control unit (not illustrated). The control unit preferably also controls the switching processes of the sample pre-compression valve 3, which has a controllable drive that is not illustrated.

Figure 2:
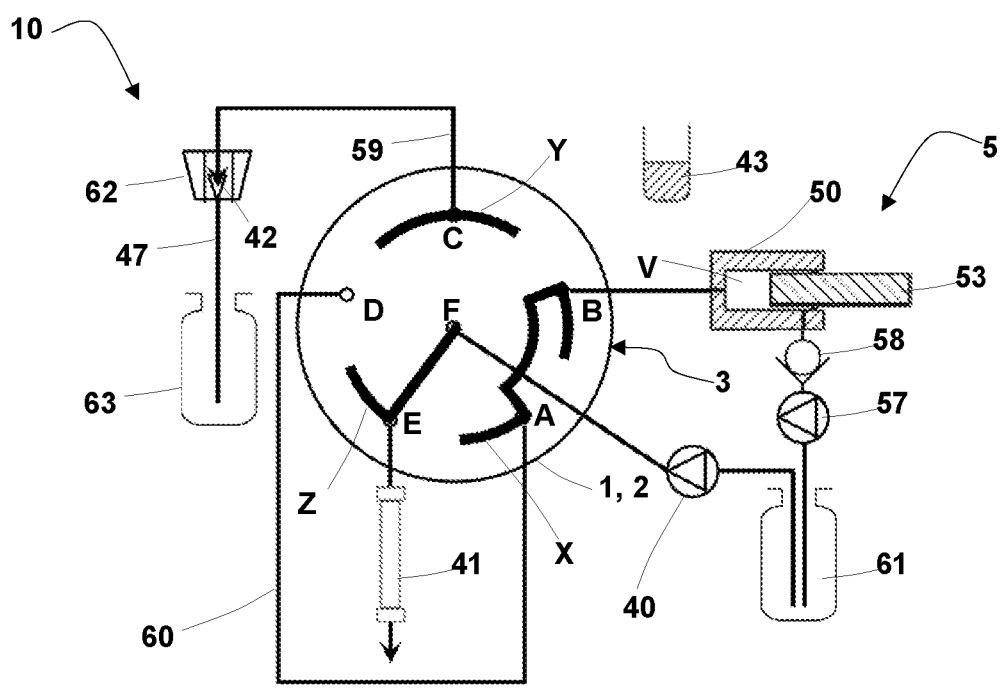
FIG. 2 is the HPLC system according to FIG. 1, whereas the sample pre-compression valve has been switched from the LOAD position to the PRESSURE COMPENSATION position.

FIG. 2 shows the sampler of the invention according to FIG. 1 in the PRESSURE COMPENSATION position, in which the groove Z still connects the solvent pump 40 with the chromatography column 41 through the ports E and F, but where the port D is closed pressure-tight, so that a pressure higher than the ambient pressure can be built up in the sample loop 60 via the groove X and the sample conveying system. This way, the pressure in sample loop 60 can be adjusted to the operating pressure on the chromatography column 41. During this step, the sample needle 42 on the end of the sample intake/discharge line 59 can be driven into the wash port 62, so that the groove Y and the line 59 with the sample needle 42 can be washed in the next step.

FIG. 3 shows the sampler of the invention according to the foregoing Figures with the sample pre-compression valve 3 in the so-called INJECT position, in which the sample can be conducted from the sample loop 60 to the chromatography column 41 not only via the grooves Z and X, but in which the sample conveying system 5, the ports B and C, the groove Y, the sample intake/discharge line 59 and the sample needle 42 can also be washed through the connection of the groove Y of the ports B and C. The latter is preferably effected in that a cleaning pump 57 is connected by a return valve 58 to the sample conveying system 5 that flushes solvent through said components into the waste tank 63.

In the process, preferably also the movable element 53 of the syringe 50 of the sample conveying system 5 is used, whereas the movable element 53 is pressed into the sample conveying system 5, so that the volume V of the sample conveying system 3 is reduced. The latter position is shown in FIG. 4.

Figure 5:
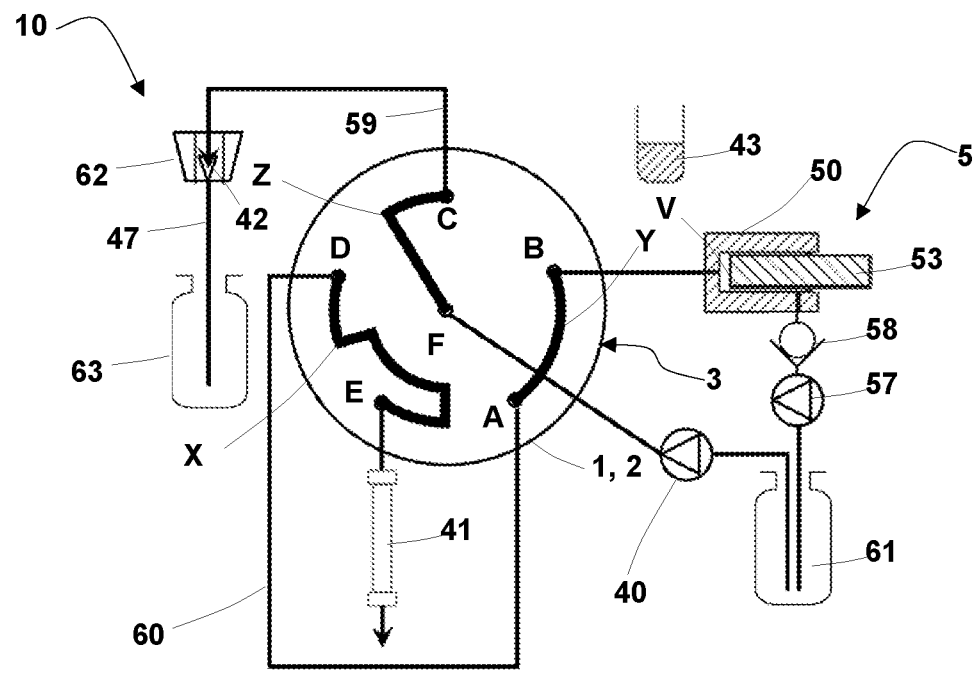
FIG. 5 is the HPLC system according to the foregoing Figures, whereas the sample pre-compression valve has been switched to the PUMP PURGE position.

FIG. 5 shows the sampler 10 according to the invention from FIGS. 1 to 4, whereas the sample pre-compression valve 3 is in the PUMP PURGE position. The groove Z connects the ports F and C here so that the solvent pump 40 can flush solvent through the groove Z, the sample intake/discharge line 59 and the sample needle 42 into the wash port 62. During this process, the sample loop 60 is excluded from the flushing process.

Figure 6:
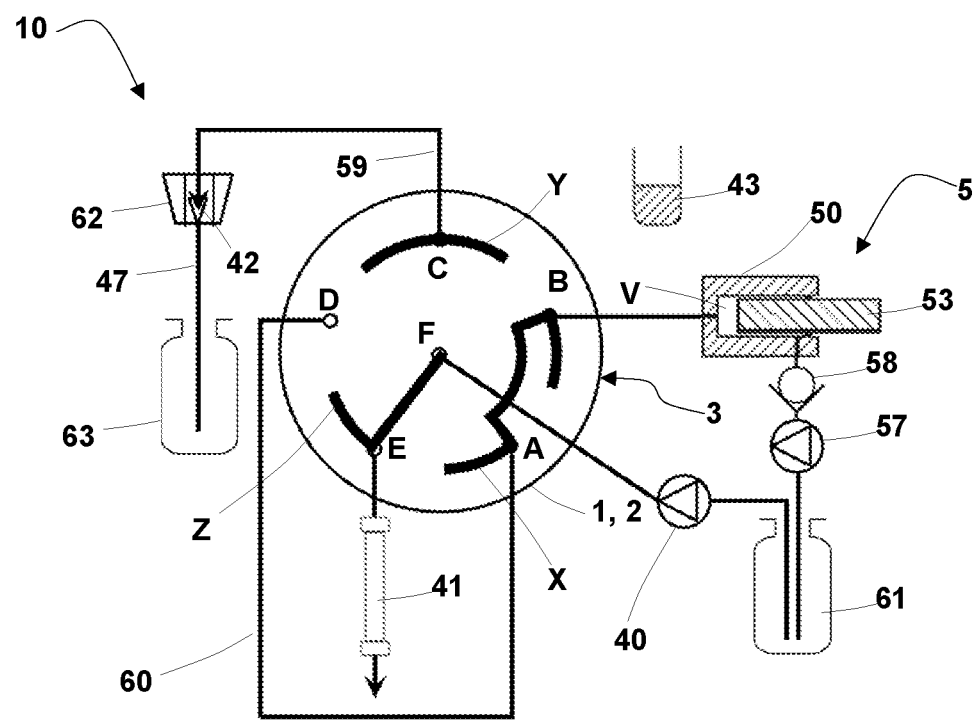
FIG. 6 is the HPLC system according to the foregoing Figures, whereas the injection valve is in the PRESSURE COMPENSATION position but the sample conveying system is decompressed (decompression part 1).

FIG. 6 shows the sampler 10 according to the invention from the foregoing Figures, whereas the sample pre-compression valve 3 is again in the PRESSURE COMPENSATION position, meanwhile this here is more an illustration of the decompression (part 1), meaning of the pressure reduction in the sample loop by the increase in the volume V of the sample conveying system.

Figure 7:
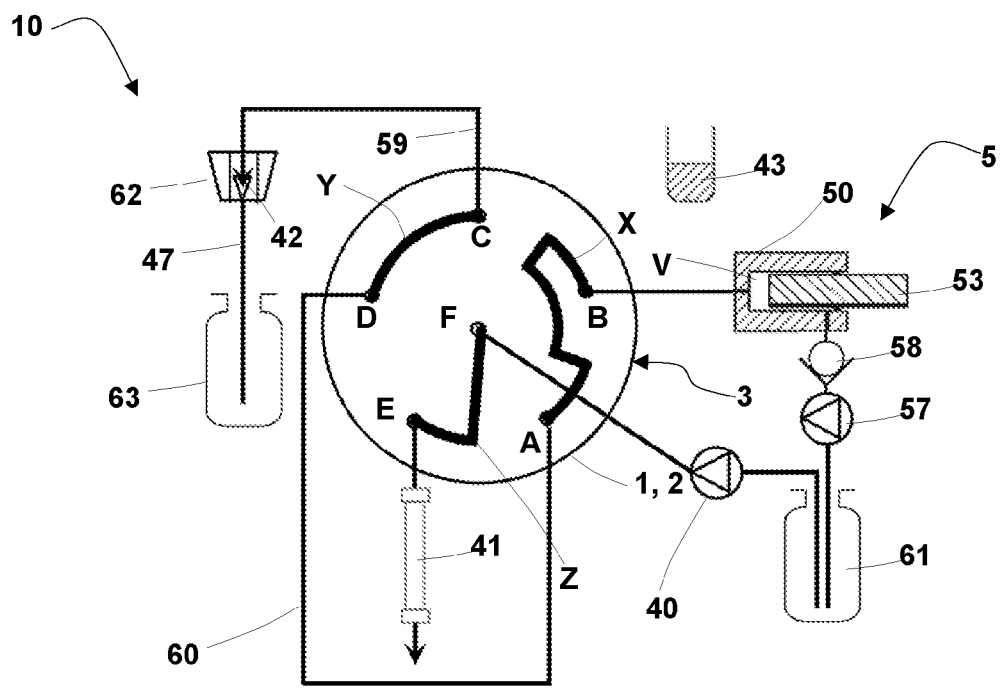
FIG. 7 is the HPLC system according to the foregoing Figures, whereas the sample pre-compression valve is in the position to take the sample (decompression part 2).

FIG. 7 shows the second part of the decompression, in which the sample pre-compression valve 3 is driven into the same position as in the LOAD position, whereas the movable element 53 of syringe 50 in the sample conveying system 5 is brought into a position that enables a repeated drawing up of a sample through the sample conveying system 5 into sample loop 60. As shown in FIG. 1, the sample needle 42 must be brought into a sample tank 43 here from the wash port 62.

Figure 8:
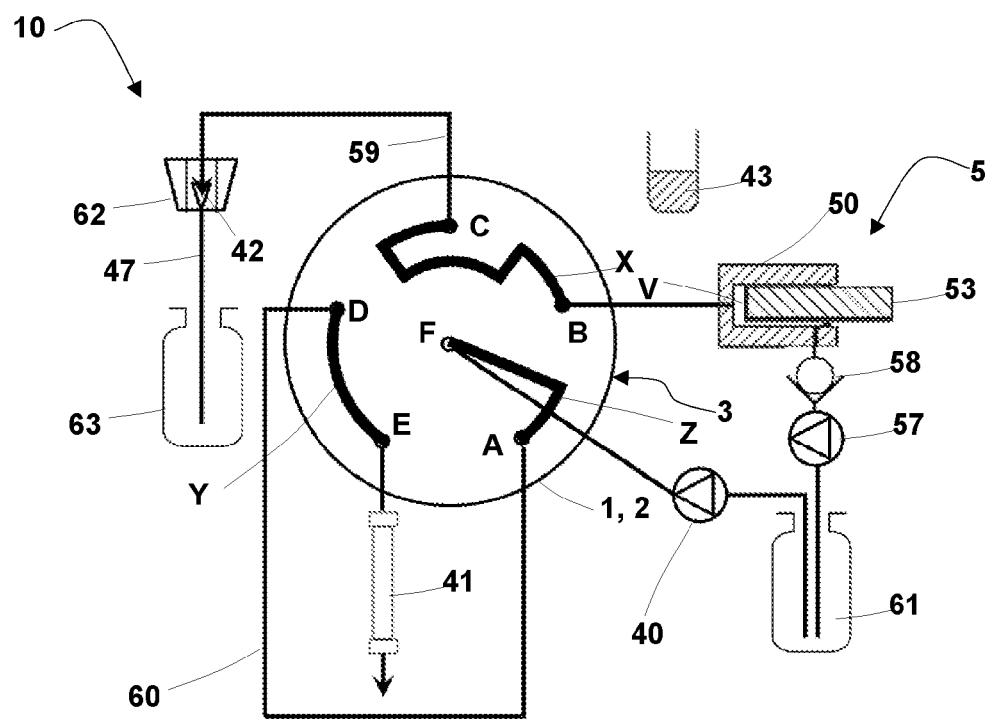
FIG. 8 is the HPLC system according to the foregoing Figures, whereas the injection valve is in an alternative INJECT position.

In alternative to the INJECT position, the sample pre-compression valve of the second embodiment can also have an alternative INJECT position, which is shown in FIG. 8. Here, the groove X connects the ports B and C, whereas the groove Y connects the ports D and E, while the groove Z connects the ports A and F. It is also possible in this way to conduct solvent from the pump 40 via the grooves Y and Z through sample loop 60 to the chromatography column 41, while the sample conveying system 5, the groove X and the sample intake/discharge line 59 as well as the sample needle 42 can be cleaned.

In the following, a sampler according to the invention with a sample pre-compression valve of the second variant is described by means of FIGS. 9 to 15.

Figure 9:
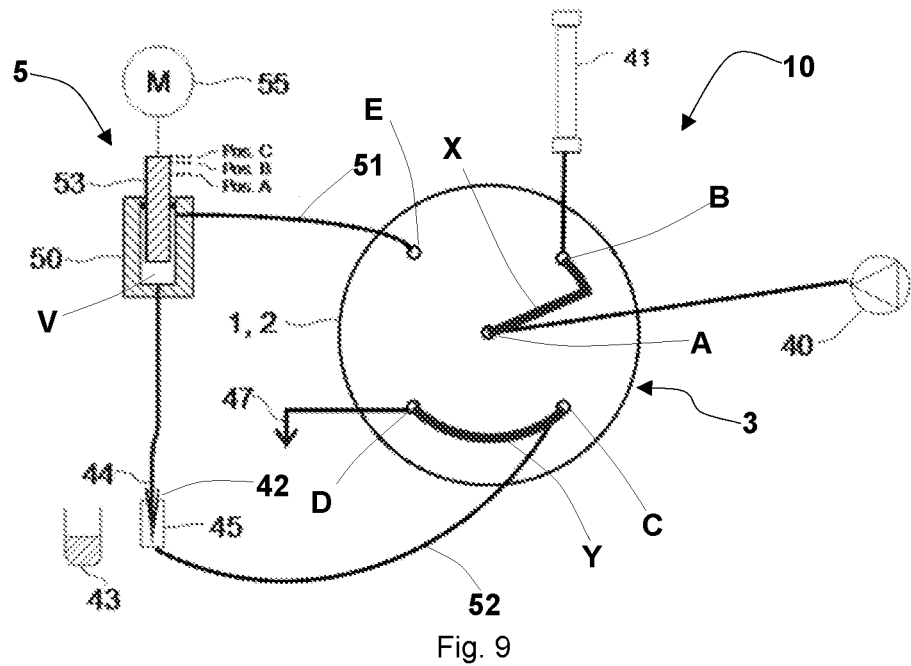
FIG. 9 is a schematic diagram of an HPLC system with a sampler according to the invention with a sample pre-compression valve of the second embodiment in the LOAD position.

FIG. 9 shows a schematic diagram of an HPLC system with a sampler 10 working according to the split-loop principle, which comprises a sample conveying system 5, an injection valve 3 and a pump, preferably a high-pressure pump 40. In addition, the sampler 10 is provided with a sample loop that consists of the first connecting piece 51 and a second connecting piece 52, 44. This can be a pressure-resistant line with small diameter, for example, in the form of glass or stainless steel capillaries. The connecting piece 51 is connected with a port E of the sample pre-compression valve 3 and with the sample conveying system 5 and respectively its pump volume V. The second connecting piece consisting of an intake part 44 and a feed part 52 is designed so that it can be disconnected. For this purpose, the feed part 52 ends in an injection port 45, which is connected with the port C of the sample pre-compression valve 3 through the feed part 52. The intake part 44 connected on one end with the pump volume V of the sample conveying system 5 is provided on the other end with a sample needle 42, whereby the intake part 44 can be connected with the injection port 45.

Figure 12:
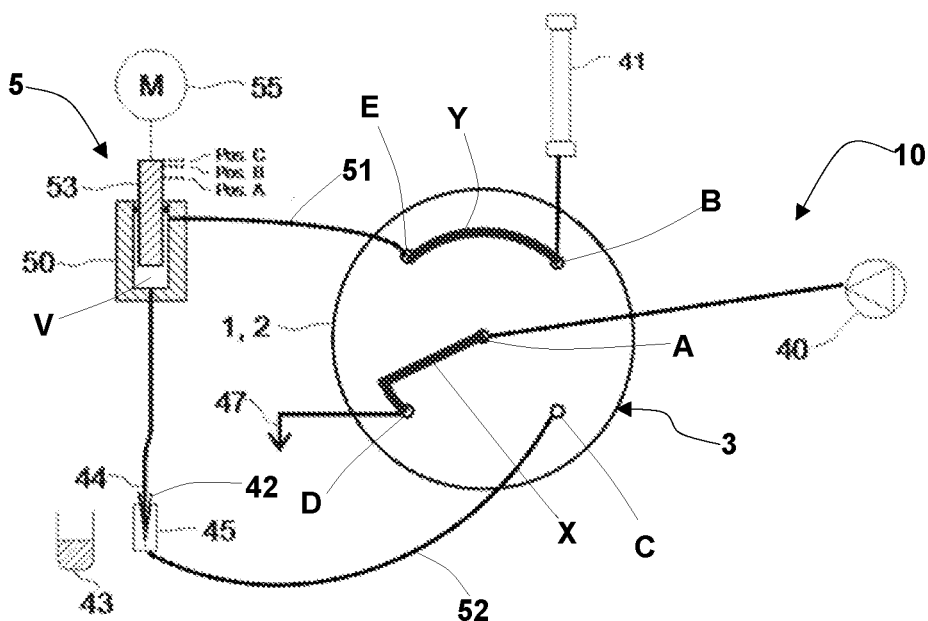
FIG. 12 is the HPLC system according to the foregoing Figures, whereas the injection valve has been switched to the PUMP PURGE position.

The sample needle 42, however, can also be moved to a sample tank 43 and from there, aspire a defined sample volume into the intake part 44 in the manner explained in the following. Furthermore, the sample needle 42 can also be moved to a tank for a cleaning fluid (not illustrated), in order to take in cleaning fluid from it into the sample conveying system 5. When the sample needle 42 is reinserted into the needle seat 45, the cleaning fluid that has been taken in through the sample loop part 51, the port E, the groove Y and the port B, which is connected with chromatography column 41, can be transported to the chromatography column when piston 53 is pressed down, for the reason that port C is closed pressure-tight (FIG. 12). This way, the chromatography column 41 can be cleaned. This cleaning procedure is conducted preferably in the PUMP PURGE position of the sample pre-compression valve, which is shown in FIG. 12.

The sample conveying system 5 comprises a syringe 50 in the illustrated embodiment, in which a piston 53 is guided pressure-tight and movable. The piston 53 is powered by means of a drive 55, for example, a step motor. The drive is preferably actuated by a control unit (not illustrated). The control unit preferably also controls the switching processes of the sample pre-compression valve 3, which has a controllable drive that is not illustrated.

The port D of the injection valve is preferably connected with a waste line 47 from which a fluid can be discharged into a waste reservoir that is not illustrated.

The high-pressure pump 40 is connected with the port A of the sample pre-compression valve. A chromatography column 41 is connected with the port B.

The sample pre-compression valve 3 is preferably comprised of a stator 1 and a rotor 2. At the same time, the stator 1 is preferably provided with the ports A, B, C, D, and E. These ports connect the sample pre-compression valve 3 with the other functional elements of the HPLC element through the connecting lines described above, which can be embodied as capillary connections. In the interest of clarity, the high-pressure screw connections required for this purpose are not shown in FIG. 9. For reasons of simplicity, the sample pre-compression valve is shown in the border area between the stator 1 and the rotor 2, whereas both the design of the front face of the stator 1 as well as the design of the front face of the stator 2 is shown, to help understand the mode of functioning. Within the sample pre-compression valve 3, the ports are preferably embodied as drill holes leading to the other side of the stator. The rotor 2, as shown in the illustration of FIG. 9, comprises at least the grooves X, and Y, which are precisely aligned on the drill holes of the entry and exit ports.

The rotor 2 is preferably pressed against the stator with pressing force, so that a common border area between the rotor 2 and the stator 1 is formed where both parts tighten against each other. The pressing force is dimensioned for this purpose in such a way that the arrangement is still tight even under the highest expected pressures.

In the LOAD position of valve 3 as shown in FIG. 9, the grooves X and Y are aligned with the ports A, B, C, D and E so that the groove Y connects the port C with port D and the groove X connects the ports A and B. In this LOAD position, the high-pressure pump 40 can thus conduct fluid in the direction toward chromatography column 41. The port E is preferably closed pressure-tight in the process. In this LOAD position, the sample can furthermore be drawn up from a sample tank 43. It is possible in addition that the sample needle 42 is driven into a sample tank 43. By moving the piston 53 upward, meaning out of the sample conveying system 5, for example, from the position A into position C (see FIG. 9), the sample from the sample tank 43 can be taken up there into the sample needle 42 and possibly also into the sample loop 44. The sample needle 42 can then be moved out of the sample tank 43 into the injection port 45 for injection after completed pressure compensation.

Figure 10:
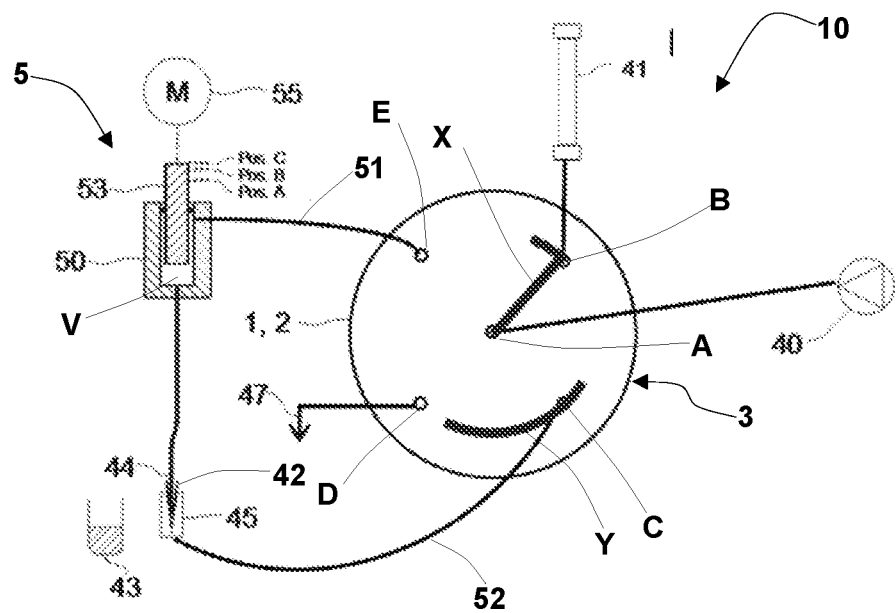
FIG. 10 is the HPLC system according to FIG. 9, whereas the injection valve has been switched from the LOAD position to the PRESSURE COMPENSATION position.

In the next step, the pressure in the sample loop is then adjusted to the system pressure of the chromatography column 41, meaning to the pressure with which the high-pressure pump 40 feeds the fluid to the inlet of the chromatography column 41. For this purpose, the sample pre-compression valve 3 is switched to a PRESSURE COMPENSATION position in which the connecting piece 51 and the second connecting piece or the feed part 52 of the sample loop are preferably not connected to the other ports of the sample pre-compression valve (FIG. 10).

In order to adjust the pressure in the sample loop 52, 44, 51 including the sample conveying system 5 to the system pressure, the piston 53 of the high-pressure resistant sample conveying system 5 can be moved out of position C into position B. So not to interrupt the flow through the chromatography column 41 while the volume required for the compression of the sample loop content is conducted, the groove X in the rotor 2 is preferably designed hook-shaped, so that the two ports A and B are also still connected while in the PRESSURE COMPENSATION position. The conveying path of the piston 53 from position C to position B that is necessary for the pressure build-up can be calculated based on the compressibility of the fluid volume trapped in the sample conveying device 5 and the sample loop, and by the elasticity of the arrangement, and the current pump pressure. In alternative, the pressure compensation can be achieved by means of a control circuit for the pressure in the high-pressure resistant sample conveying system. For this purpose, the pressure must be measured at a suitable point and the position of the piston 53 in the sample conveying system 5 must be set in such a way by the drive 55, so that the pressure equals the necessary target pressure (=column pressure). For the pressure measurement, a pressure sensor or indirectly, a force measurement can be used. A force measurement on the piston 53 or in the drive 55 are feasible solutions. Once pressure equivalence is reached, the valve can be switched to an INJECT position and the aspired sample volume can thereby be injected into the column 41

Figure 11:
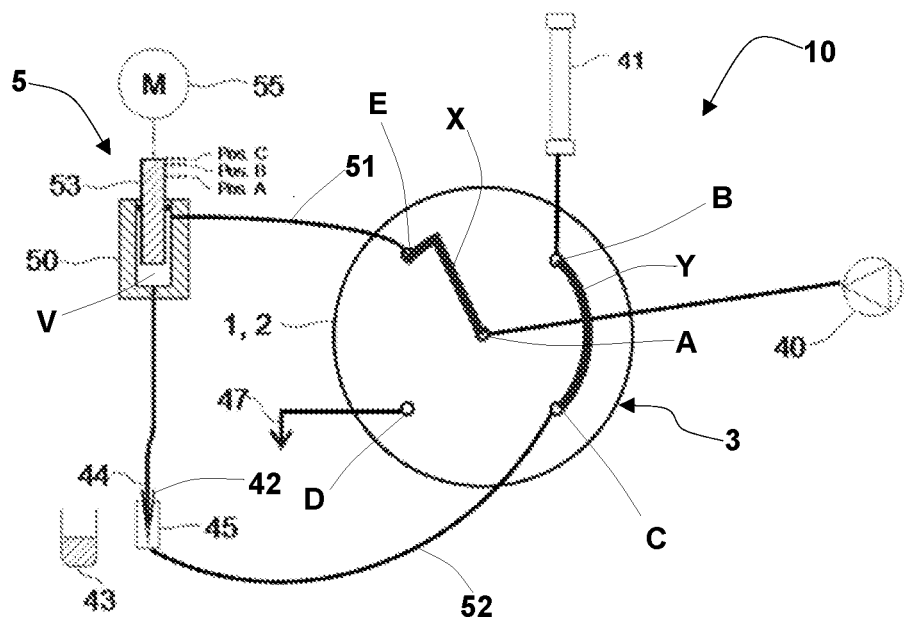
FIG. 11 is the HPLC system according to FIG. 9 and FIG. 10, which has been switched to the INJECT position.

(FIG. 11). This applies in the same way also to the embodiments shown in FIGS. 1 to 8. The sample volume to the column is preferably conducted by means of the pump flow and notably, through the sample loop part 52, the port C, the groove Y and the port B.

A control unit (not illustrated) can measure the force that the drive 55 has to exert in order to reach a corresponding compression in the sample loop. The drive 55 can be provided with an integrated sensor (not shown) for this purpose, the signal of which is fed to the control unit. The control unit can thereby determine the actual pressure in the pump volume and thus in the sample loop (the pressure drop in the connecting pieces and the valve is negligibly small) and can regulate it to the desired value. This applies in the same way also to the embodiments shown in FIGS. 1 to 8.

After the aspired sample volume has been completely conveyed from the intake part 44 to the column 41 through the fluid conveyed by the pump 40, the valve for decompression of the sample loop can be switched directly into the PRESSURE COMPENSATION position again (FIG. 10).

Before the injection valve is moved out of the PRESSURE COMPENSATION position back into the LOAD position, the piston 53 is preferably moved into position C. The pressure in the sample loop is thereby adjusted to the atmospheric pressure. During this decompression time, the column 41 is already connected with the pump 40 in the PRESSURE COMPENSATION position of the injection valve 3, due to the hook-shaped design of the groove X, in order to avoid pressure changes. The conveying path of the piston 53 from position B to position C can be determined, in the same way as for the compression, by calculation or by measurement and control of the pressure. In alternative, the pressure can also be determined indirectly by means of a force measurement on the piston 53 or the drive 55 of the piston.

Once the decompression of the sample loop is completed, the valve 3 is set to the LOAD position. In the process, neither any harmful flows occur in the sample pre-compression valve nor any damages on the chromatography column that are caused by pressure changes. The same also applies to the compression step. The piston 53 of the high-pressure resistant sample conveying system 5 can now be driven again to the initial position A. The excess fluid quantity is disposed through the waste connection 47, the pressure-less sample needle 42 can thereafter be moved out of the needle seat of the injection port 45 to the corresponding sample flask for drawing up the next sample.

The position C in the decompression can also differ from the initial position C before the compression. If, for example, gradients (time-controlled admixture ratio of the mobile phase) are pumped through the column, position C at the end of the decompression can be a different one, because the compressibility of the loop content may have changed as applies.

The mentioned control unit can store the predefined positions A, B, C and/or path differences between these positions in dependency on parameters of the complete sampler, in particular of the mobile phase compressibility, elasticity characteristics of the sample loop and the sample conveying system, etc. These positions can then be actuated specifically (meaning without a control unit) or they can serve as approximate values of the initial values for a controlled movement. To determine the positions A, B, C or the movement paths for the piston, a switching process of the sample pre-compression valve 3 can be conducted without compression or decompression. By means of a pressure sensor, the pressure drop can then be identified, and the required path and respectively the relevant position B and respectively C can then be determined from it. The values determined this way can then be stored and used for further switching processes in application of a compression or decompression. A corresponding sensor can also be provided in the pump 40. This is bearing in mind that pumps of this kind for the HPLC always have a pressure sensor anyway for the control of the conveyed mobile phase. Likewise, the compressibility of the medium, in particular of the mobile phase, can be determined by means of the pump 40. Pumps of this kind are designed, for example, as double-piston pumps, whereas the switching from one piston to another is suitably activated or controlled by means of a pressure sensor and a control unit, in such a way so that a highly constant flow rate results. As the compressibility of the medium must be considered for this switching process, the suitable actuation of the (double-piston) pump when switching from one piston to another can serve as the basis for determining the compressibility, which can then be supplied to the control unit as information. This applies in the same way also to the embodiments shown in FIGS. 1 to 8.

With the presented automatic sampler, it is therefore ensured that before the intake part 44 is connected in the liquid path to the chromatography column 41, meaning before the sample pre-compression valve 3 is switched to the INJECT position, the sufficiently (high) pressure resistant sample conveying system 5, adjusts the pressure in the sample loop to the current system pressure in the chromatography column 41 by compression in a special intermediate position of the sample pre-compression valve, namely the PRESSURE COMPENSATION position.

Furthermore, before the sample loop is disconnected for taking in a sample volume from a sample tank 43, meaning before the sample pre-compression valve 3 is switched to the LOAD position, the pressure in the sample loop is adjusted to the atmospheric pressure (decompression) by the volume change in the sample conveying system 5, preferably in the same intermediate position of the sample pre-compression valve 3, namely the PRESSURE COMPENSATION position.

FIG. 12 shows the sampler 10 according to the invention with the sample pre-compression valve 3 in the PUMP PURGE position. In this position, the groove X connects the ports A and D, so that the line from the port A to the pump 40, the groove X and the port D can be flushed with the aspired fluid from the pump 40. The flushed fluid as well as solvent residues are disposed out of the waste line 47 in this process.

Figure 13:
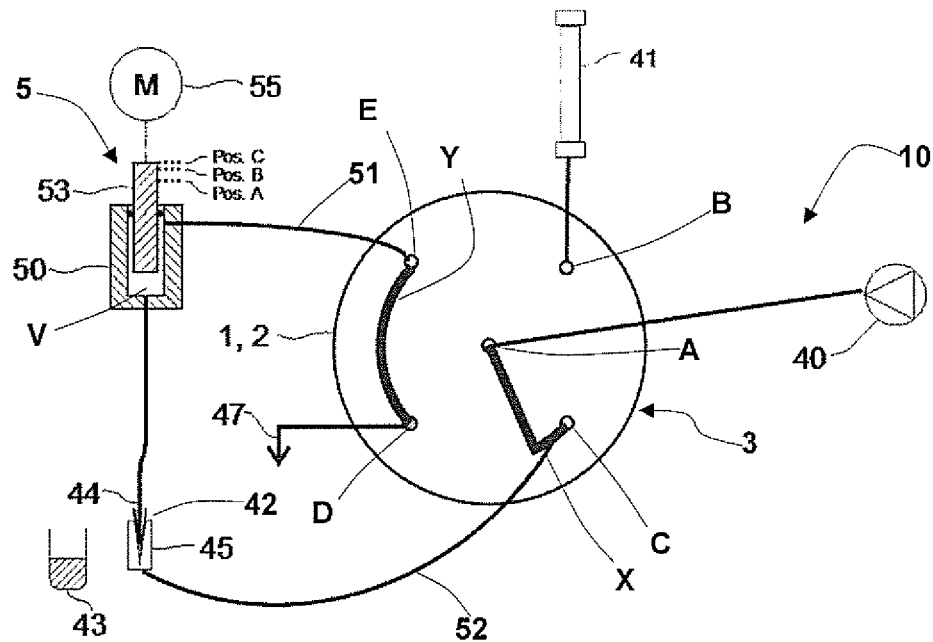
FIG. 13 is the HPLC system according to the foregoing Figures, whereas the injection valve has been switched to the FULL PURGE position.

FIG. 13 shows the sampler 10 according to the invention with the sample pre-compression valve 3 in the FULL PURGE position. In this position, the groove X connects the ports A and C, and the groove Y connects the ports D and E, so that the line from the port A to the pump 40, the groove X, the port C, the feed part 52, the sample needle 42, the needle seat 45, the intake part 44, the sample conveying system 5, the sample loop part 51, the port E, the groove Y and the port D can be flushed with the aspired fluid from pump 40. The flushed fluid is purged in the waste line 47 in this process.

Figure 14:
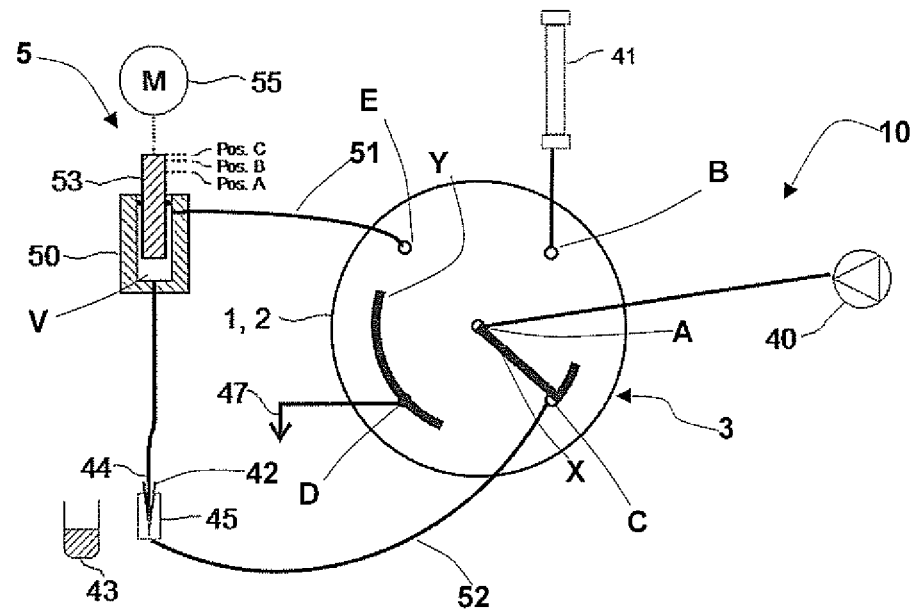
FIG. 14 is the HPLC system according to the foregoing Figures, whereas the injection valve has been switched to the UNDERPRESSURE position.

FIG. 14 shows the sampler 10 according to the invention with the sample pre-compression valve 3 in the UNDERPRESSURE position. In this position, the groove X connects the port A with the port C. Furthermore, the port E, the port B and the port D are not connected with any other port in this position. The sample needle 42 is preferably arranged in the needle seat 45, so that pulling out the piston 53 of the sample conveying system 5 can create an underpressure in the sample loop 51, 44, 52, the groove X that connects the ports A and C with each other, and the connecting line from the port A to pump 40. It is possible in this way to overcome the hydrostatic column of the solvent and to support the pump 40 in aspiring the solvent. In addition, for example, before the FULL PURGE position or the PUMP PURGE position, gas bubbles can be removed from the device by switching to the UNDERPRESSURE position and thereby creating the underpressure. This preferably takes place while the pump 40 has a lower conveying capacity than created by the underpressure of the sample conveying system or while the pump is shut off.

Figure 15:
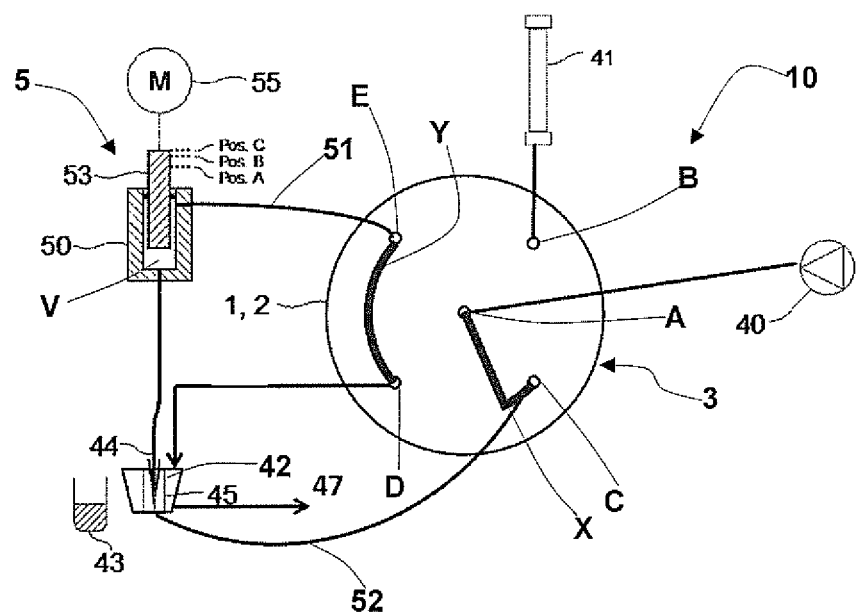
FIG. 15 is the HPLC system according to FIG. 13 in the FULL PURGE position with additional connecting line from the waste port to the wash port of the needle seat.

FIG. 15 shows a preferred embodiment according to the invention, wherein everything is arranged as shown in FIG. 13, with the sole exception that the line from the port D is led to a wash port of the needle seat and the waste drain 47 is arranged on the wash port of the needle seat 45. This way, the cleaning agent can be conducted into the wash port of the needle seat during flushing in the FULL PURGE position and thus, the sample needle 42 is also rinsed from the outside. In the process, the needle is preferably slightly driven out of the needle seat, so that the cleaning agent can reach the wash port of the needle seat for the exterior cleaning of the sample needle and then be purged from the wash port into the waste.

The following reference signs are used in FIGS. 1-15.
A Port in stator
B Port in stator
C Port in stator
D Port in stator
E Port in stator
F Port in stator
X Groove in rotor
Y Groove in rotor
Z Groove in rotor
1 Stator
2 Rotor
3 Sample pre-compression valve
5 Sample conducting device
10 Sampler
40 Solvent pump(s), preferably high-pressure pump(s)
41 Chromatography column
42 Sample needle
43 Sample tank
44 Intake part
45 Injection port/Needle seat
47 Waste line
50 Syringe
51 Sample loop part
52 Sample loop part or feed part
53 Movable element
55 Controllable drive
57 Cleaning pump
58 Return valve
59 Sample intake/discharge line
60 Sample loop
61 Solvent bottle
62 Wash port
63 Waste tank
V Volume

What is claimed is:

1. A sample pre-compression valve for liquid chromatography, the sample pre-compression valve comprising:
(a) a stator; and
(b) a rotor, in which a face surface of the rotor is configured to be rotated against a face surface of the stator, in which the stator comprises at least five ports, the at least five ports including a first port, a second port, a third port, a fourth port, and a fifth port, the rotor comprises at least a first groove and a second groove, in which the first groove is configured to connect to two of the at least five ports, and in which the second groove is configured to connect to a different two of the at least five ports,
(i) in a LOAD position of the sample pre-compression valve, the first groove connects the first port and the second port such that the first groove does not have a dead volume, and the second groove either connects or does not connect to the third port and the fourth port;
(ii) in a PRESSURE COMPENSATION position of the sample pre-compression valve, the first groove connects the first port and the second port such that the first groove does have the dead volume, and the second groove either connects or does not connect the third port and the fourth port; and
(iii) in an INJECT position of the sample pre-compression valve, the first groove connects the first port and the fifth port such that the first groove does not have the dead volume, and the second groove either connects or does not connect the second port and the third port.

2. The sample pre-compression valve according to claim 1, wherein
(i) the first and second ports are arranged on one or two circular paths around a center of a circular-shaped stator; or
(ii) the first port is arranged at the center of the circular-shaped stator and the second port is on a circular path around the center of the circular-shaped stator.

3. The sample pre-compression valve according to claim 2, wherein the first and the second ports are arranged on one or more circular paths around the center of the circular-shaped stator, in which the stator further includes a sixth port that is arranged at the center of the circular-shaped stator.

4. The sample pre-compression valve according to claim 2, wherein the third, the fourth, and the fifth ports are arranged on the one or two circular paths around the center of the circular-shaped stator.

5. The sample pre-compression valve according to claim 3, wherein the rotor further includes a third groove configured to connect the sixth port with one of the first, the second, the third, the fourth, or the fifth ports.

6. The sample pre-compression valve according to claim 5, wherein in the LOAD position, the third groove connects the fifth port and the sixth port such that the third groove does not have a dead volume; wherein in the PRESSURE COMPENSATION position, the third groove connects the fifth port and the sixth port such that the third groove does have the dead volume; and wherein in the INJECT position, the third groove connects the fourth port and the sixth port such that the third groove does not have the dead volume.

7. The sample pre-compression valve according to claim 6, wherein in a PUMP PURGE position of the sample pre-compression valve, the second groove connects the first port and the second port.

8. The sample pre-compression valve according to claim 7, wherein in the PUMP PURGE position of the sample pre-compression valve, the first groove connects the fourth port and the fifth port such that the first groove does not have the dead volume.

9. The sample pre-compression valve according to claim 8, wherein in the PUMP PURGE position of the sample pre-compression valve, the third groove connects the third port and the sixth port such that the third groove does not have the dead volume.

10. The sample pre-compression valve according to claim 9, wherein in an alternative INJECT position of the sample pre-compression valve, the first groove connects the second port and the third port such that the first groove does not have the dead volume, and the second groove connects or does not connect to the fourth port and the fifth port.

11. The sample pre-compression valve according to claim 10, wherein in the alternative INJECT position of the sample pre-compression valve, the second groove connects the fourth port and the fifth port and the third groove connects the first port and the sixth port.

12. The sample pre-compression valve according to claim 1, wherein the second groove connects the third port and the fourth port in the LOAD position; wherein the second groove does not connect the third port and the fourth port in the PRESSURE COMPENSATION position; and wherein the second groove connects the second port and the third port in the INJECT position.

13. The sample pre-compression valve according to claim 1, wherein the first, the second, the third, the fourth, and the fifth ports are arranged on a same circular path around the center of the circular-shaped stator; or the second, the third, the fourth, and the fifth ports are arranged on the same circular path around the center of the circular-shaped stator and that the first port is arranged at the center of the circular-shaped stator.

14. The sample pre-compression valve according to claim 1, wherein the first port is arranged at a center of the circular-shaped stator and the second port, third port, the fourth port, and the fifth port are arranged on one or more circular paths around the center of the circular-shaped stator.

15. The sample pre-compression valve according to claim 1, wherein in the LOAD position and the PRESSURE COMPENSATION position, the fifth port is not connected to the first groove, and the fifth port is not connected to the second groove.

16. The sample pre-compression valve according to claim 1, wherein in the PRESSURE COMPENSATION position and the INJECT position, the fourth port is not connected to the first groove, and the fifth port is not connected to the second groove.

17. The sample pre-compression valve according to claim 1, wherein in which the at least five ports have a point-shape or a groove-shape.

18. A method of injecting a sample into a chromatography column, the method comprising: pre-compressing a sample with a sample pre-compression valve, the sample pre-compression valve comprising:
  (a) a stator; and
  (b) a rotor, in which a face surface of the rotor is configured to be rotated against a face surface of the stator, in which the stator comprises at least five ports, the at least five ports including a first port, a second port, a third port, a fourth port, and a fifth port, the rotor comprises at least a first groove and a second groove, in which the first groove is configured to connect to two of the at least five ports, and in which the second groove is configured to connect to a different two of the at least five ports,
    (i) in a LOAD position of the sample pre-compression valve, the first groove connects the first port and the second port such that the first groove does not have a dead volume, and the second groove either connects or does not connect to the third port and the fourth port;
    (ii) in a PRESSURE COMPENSATION position of the sample pre-compression valve, the first groove connects the first port and the second port such that the first groove does have the dead volume, and the second groove either connects or does not connect the third port and the fourth port; and
    (iii) in an INJECT position of the sample pre-compression valve, the first groove connects the first port and the fifth port such that the first groove does not have the dead volume, and the second groove either connects or does not connect the second port and the third port.

19. A sampler for liquid chromatography comprising:
(A) a sample pre-compression valve including:
  (a) a stator; and
  (b) a rotor, in which a face surface of the rotor is configured to be rotated against a face surface of the stator, in which the stator comprises at least five ports, the at least five ports including a first port, a second port, a third port, a fourth port, and a fifth port, the rotor comprises at least a first groove and a second groove, in which the first groove is configured to connect to two of the at least five ports, and in which the second groove is configured to connect to a different two of the at least five ports,
    (i) in a LOAD position of the sample pre-compression valve, the first groove connects the first port and the second port such that the first groove does not have a dead volume, and the second groove either connects or does not connect to the third port and the fourth port;
    (ii) in a PRESSURE COMPENSATION position of the sample pre-compression valve, the first groove connects the first port and the second port such that the first groove does have the dead volume, and the second groove either connects or does not connect the third port and the fourth port; and
    (iii) in an INJECT position of the sample pre-compression valve, the first groove connects the first port and the fifth port such that the first groove does not have the dead volume, and the second groove either connects or does not connect the second port and the third port;
  wherein the first and the second ports are arranged on one or more circular paths around the center of the circular-shaped stator, in which the stator further includes a sixth port that is arranged at the center of the circular-shaped stator;
(B) a sample conveying system;
(C) a sample intake/discharge line;
(D) a sample loop;
(E) a solvent pump; and
(F) a chromatography column, wherein the first port is connected to the fourth port through the sample loop, the second port is connected to the sample conveying system, the third port is connected with the sample intake/discharge line, the fifth port is connected to the chromatography column, and the sixth port is connected to the solvent pump.

20. A sampler for liquid chromatography comprising:
(A) a sample pre-compression valve including:
  (a) a stator; and
  (b) a rotor, in which a face surface of the rotor is configured to be rotated against a face surface of the stator, in which the stator comprises at least five ports, the at least five ports including a first port, a second port, a third port, a fourth port, and a fifth port, the rotor comprises at least a first groove and a second groove, in which the first groove is configured to connect to two of the at least five ports, and in which the second groove is configured to connect to a different two of the at least five ports, (i) in a LOAD position of the sample pre-compression valve, the first groove connects the first port and the second port such that the first groove does not have a dead volume, and the second groove either connects or does not connect to the third port and the fourth port;

(ii) in a PRESSURE COMPENSATION position of the sample pre-compression valve, the first groove connects the first port and the second port such that the first groove does have the dead volume, and the second groove either connects or does not connect the third port and the fourth port; and (iii) in an INJECT position of the sample pre-compression valve, the first groove connects the first port and the fifth port such that the first groove does not have the dead volume, and the second groove either connects or does not connect the second port and the third port;

(B) a sample loop including a sample conveying system and a needle seat;

(C) a discharge line;

(D) a solvent pump; and (E) a chromatography column, wherein the first port is connected to the solvent pump, the second port is connected to the chromatography column, the third port is connected to the sample loop, and the fourth port is connected to the discharge line.

* * * * *